United States Patent [19]
Tjulkov et al.

[11] Patent Number: 4,832,022
[45] Date of Patent: May 23, 1989

[54] CRYOGENIC ULTRASONIC SCALPEL

[75] Inventors: Gennady I. Tjulkov; Boris I. Alperovich; Ljutsia M. Paramonova; Valery I. Soloviev; Alexandr I. Paramonov, all of Tomsk, U.S.S.R.

[73] Assignees: Tomsky Gosudarstvenny Universitet IM. Kuibysheva; Tomsky Gosudarstvenny Meditsinsky Institut, both of Moscow, U.S.S.R.

[21] Appl. No.: 44,894

[22] Filed: Apr. 30, 1987

[30] Foreign Application Priority Data

May 26, 1986 [SU] U.S.S.R. .................. 4067037

[51] Int. Cl.[4] ............................................. A61B 17/36
[52] U.S. Cl. ..................... 128/303.1; 128/DIG. 27
[58] Field of Search .......... 128/24 A, 303.1, 399–402, 128/DIG. 27

[56] References Cited

U.S. PATENT DOCUMENTS

| 3,636,943 | 1/1972 | Balamuth | 128/303.1 |
|---|---|---|---|
| 3,786,814 | 1/1974 | Armao | 128/303.1 |
| 3,918,442 | 11/1975 | Nikolaev et al. | 128/303.1 |
| 3,942,519 | 3/1976 | Shock | 128/303.1 |
| 4,528,979 | 7/1985 | Marchanko et al. | 128/303.1 |
| 4,609,368 | 9/1986 | Dotson | 128/24 A |
| 4,724,834 | 2/1988 | Alperovich et al. | 128/303.1 |

FOREIGN PATENT DOCUMENTS

| 460869 | 4/1975 | U.S.S.R. | 128/303.1 |
|---|---|---|---|
| 825056 | 5/1981 | U.S.S.R. | 128/303.1 |

Primary Examiner—Max Hindenburg
Attorney, Agent, or Firm—Burgess, Ryan & Wayne

[57] ABSTRACT

Disclosure is made of a cryogenic ultrasonic scalpel comprising a housing, an ultrasonic source installed in said housing, a cutting means to which ultrasonic vibrations are supplied from the ultrasonic source via a transformer, a tubular heat exchanger featuring inlet and outlet pipes for the supply and removal of the refrigerant and providing the required low-temperature action on the tissue being dissected, and thermal insulation between said cutting means and said tubular heat exchanger.

33 Claims, 5 Drawing Sheets

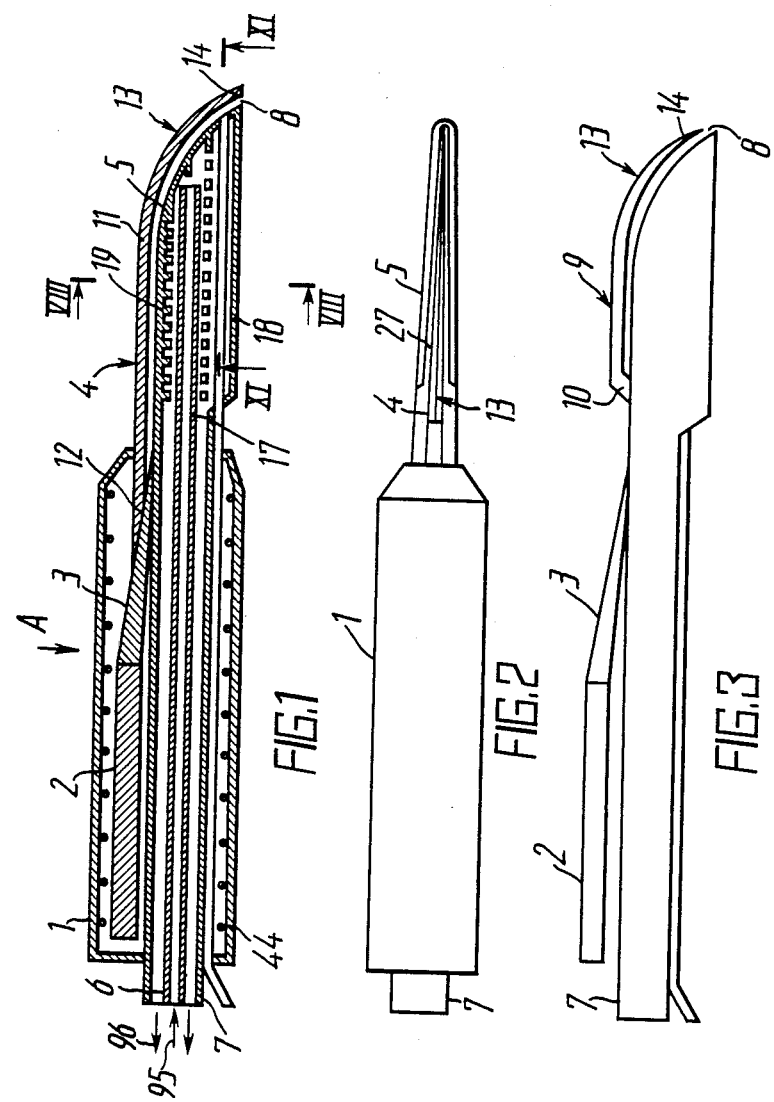

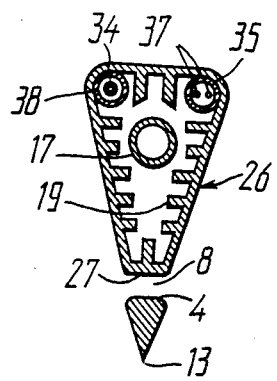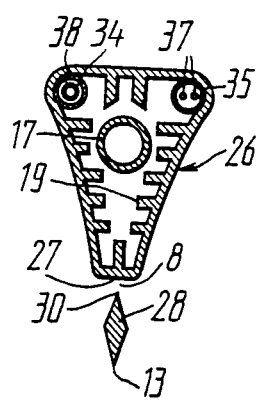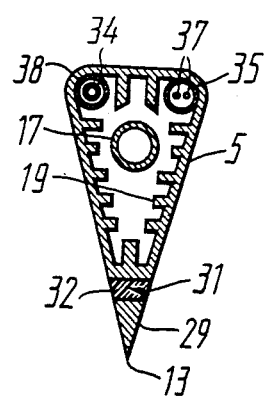
FIG.8　　　　FIG.9　　　　FIG.10
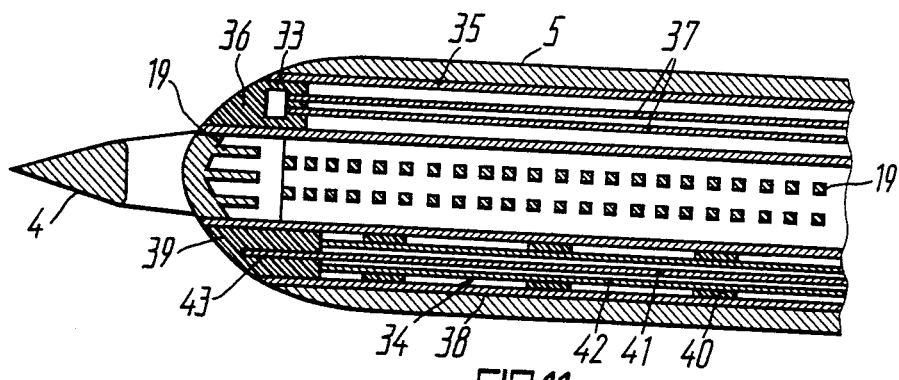
FIG.11

CRYOGENIC ULTRASONIC SCALPEL

FIELD OF THE INVENTION

This invention relates to surgical instruments and, in particular, to cryogenic ultrasonic scalpels.

The present invention can be used for surgical operations on soft tissues and parenchymal organs, such as liver, pancreas, kidneys, lungs, spleen, and in neurosurgery.

BACKGROUND OF THE INVENTION

There are known cryogenic surgical instruments comprising a device connecting a working member and a source of ultrasonic vibrations, a jacket for refrigerant circulation, which is disposed between the base of the instrument and the ultrasonic source, and a calibrated prefice in the inlet for the refrigerant (Su, A, 460 869). This instrument is deficient in that it cannot be used for surgical operations because it cannot dissect tissues.

Known in the art is a cryogenic ultrasonic scalpel comprising a housing accomodating a source of ultrasonic vibrations, a blade connected to this ultrasonic source via a transformer, and a tubular heat exchanger for supplying and bleeding the refrigerant to and from the blade. The heat exchanger is a U-shaped tube installed in thermal contact with a lateral surface of the blade and connected to refrigerant inlet and outlet pipes by bellows located in the standing wave zone formed zone at the junction of the blade with the ultrasonic source, the tubes of the heat exchanger being made narrowing in the direction of the cutting edge of the scalpel (SU, A, 825 056).

This cryogenic ultrasonic scalpel is deficient in that the speed of dissection of soft and parenchymal tissues is inadequately low and the hemostatic effect is insufficient.

A low dissection speed is due to the fact that in prior art cryogenic ultrasonic scalpels the cutting device has a negative temperature when in operation. This means that when tissue is dissected the cutting action of the scalpel is only due to the ultrasonic effect and the expected cutting action of dissecting a hard layer of tissue froze by the previous dissection is not realized. The dissection speed is low also because the refrigerating capacity is insufficient and the blade is cooled unsymmetrically, since refrigeration is from the U-shaped heat exchanger whereby the lateral surface of the blade, which is closer to the inlet, is cooled more than the other lateral surface thereof, the temperature of the refrigerant in the outlet being higher. This may cause sticking of tissue to the cutting tool and the heat exchanger. In addition, the scalpel blade has a thermal contact with the ultrasonic transformer which is a powerful heat source and this only adds to the unsymmetrical cooling of the blade. The heat from this ultrasonic transformer also contributes to raising the temperature of the scalpel blade and is, therefore, the reason of refrigeration shortage during tissue dissection. The speed of tissue dissection becomes still slower and the hemostatic effect is decreased, which prolongs the operation period quite substantially.

Moreover, the U-shaped heat exchanger wherein refrigerant inlets and outlets are set wide apart makes the instrument bulky and inconvenient.

In addition, prior art cryogenic ultrasonic scalpels have no capability to control the level of ultrasonic and low-temperature effects on the dissected tissue, which makes the instrument less efficient. Since the level of the low-temperature action cannot be monitored, the hemostatic effect may be insufficient during an operation or become the cause of post-operational necrosis of tissues in the organ being operated.

The absence of means for monitoring the level of ultrasonic action is the cause of injury to the organ being operated, e.g. by too a high temperature of the dissected tissue added to the intensive ultrasonic action.

SUMMARY OF THE INVENTION

It is an object of the invention to provide a cryogenic ultrasonic scalpel wherein ultrasonic and low-temperature actions can be applied to the tissue being dissected separately in space and successively in time.

Another object of the invention is to provide a cryogenic ultrasonic scalpel which can help shorten the duration of the operation.

Still another object of the invention is to increase the rate of the low-temperature action on the tissue being dissected during the operation.

One more object of the invention is to increase the level of ultrasonic action on the tissue being dissected.

Yet another object of the invention is to provide a cryogenic ultrasonic scalpel whereby tissue can be dissected at different angles of said scalpel to the surface of tissue being dissected.

A further object of the invention is to provide a surgical instrument capable of dissecting tough portions of pathological tissue.

A still further object of the invention is to reduce losses of ultrasonic power.

It is an object of the invention to reduce consumption of the refrigerant.

Another object of the invention is to provide a surgical instrument capable of dissecting tissue to the depth equal to the length of the cutting device.

Still another object of the invention is to provide a uniform low-temperature effect on the tissue being dissected.

It is an object of the invention to provide a cryogenic ultrasonic scalpel capable of dissecting tissue portions having different toughness and different blood supply.

It is an object of the invention to provide a surgical instrument whose housing temperature feels normal for an operator.

It is an object of the invention to provide an instrument whose low-temperature action on the tissue being dissected can be controlled.

It is an object of the invention to provide an instrument adapted for automatic maintenance of desired ultrasonic and low-temperature conditions during dissection of tissue.

These and other objects of the invention are attained in a cryogenic ultrasonic scalpel comprising, according to the invention, a housing, an ultrasonic source installed in said housing, a cutting device to which ultrasonic vibrations are supplied from said ultrasonic source via a transformer, a tubular heat exchanger featuring refrigerant inlet and outlet pipes and ensuring a low-temperature action on the tissue being dissected, and thermal insulation between the cutting device and the heat exchanger.

It is advisable that the cutting device should be made as a plate or hook having a cutting edge and secured on the tubular heat exchanger by one or both ends thereof so that a gap is provided between the cutting device and the surface of the heat exchanger for mutual thermal insulation.

It is also advisable that the cutting device having a cutting edge should be secured on the transformer or made as a unit together with the transformer from the same material, the cutting device, the transformer, and the ultrasonic source forming a single unit disposed at a distance from the tubular heat exchanger and its pipes for their mutual thermal insulation.

It is reasonable that elements should be installed inside the tubular heat exchanger to make the surface of heat exchange with the refrigerant larger; the ratio of the thickness of each element to the length thereof should be selected from a range from 0.1 to 0.2, while the ratio of the total area of the lateral surfaces of all elements to the area of the internal surface of the tubular heat exchanger should be selected from a range from 2 to 5.

It is also reasonable that a heating element should be installed on the transformer to maintain a positive temperature, in degrees celsius, of the cutting device.

It is advisable, in order to make it possible to dissect tissue portions having different toughness and different blood supply by the cryogenic ultrasonic scalpel, that the gap between the cutting device and the tubular heat exchanger should be adjustable, and, to this end, the cutting device should be equipped with a unit for moving it in relation to the tubular heat exchanger.

It is advisable that the housing of the cryogenic ultrasonic scalpel should be provided with a heating element which can keep the temperature of said housing comfortable for an operator irrespective of the low-temperature effect of the tubular heat exchanger on said housing.

It is advisable that the cutting device should be equal in length or even longer than the tubular heat exchanger.

It is advisable that the cutting device thickness should vary throughout its length.

It is advisable that the tubular heat exchanger cross-section should be shaped as a trapezium whose lesser base faces the cutting device and repeats, longitudinally, the shape of the cutting device.

It is advisable that the side surfaces of the cutting device should be continuations of the side surfaces of the tubular heat exchanger, the interaction of the two surfaces forming the cutting edge of the cutting device.

It is advisable that the thermal insulation gap between the cutting device and the tubular heat exchanger should be selected from a range from 0.5 mm to 4 mm.

It is advisable that the edge of the cutting device on the side opposite to the cutting edge should be tapered.

It is advisable a layer of plastic material having heat-insulating and water-repelling properties should be placed between the cutting device and the tubular heat exchanger in order to ensure thermal insulation.

In order to maintain a constant distance between the tubular heat exchanger and the cutting device, the cryogenic ultrasonic scalpel may be equipped with a fixing element made of a heat-insulating material and disposed on the outlet pipe for bleeding the refrigerant at a distance from the ultrasonic source, which is selected on the basis of the following relationship:

$$l = \frac{\lambda(2n-1)}{4};$$

where $l$ is the distance between the ultrasonic source and the fixing element, $\lambda$ is the ultrasonic wavelength in the transformer and cutting device, $n$ is the number of ultrasonic half-waves contained in the transformer and cutting device to the place where the fixing element is installed.

It is advisable that the cryogenic ultrasonic scalpel be equipped with a temperature sensor of the tubular heat exchanger in the zone of contact with the tissue being dissected, which should be located inside a pipeline which is hermetically sealed inside the tubular heat exchanger throughout its length on a wall opposite to the cutting device.

It is advisable that the cryogenic ultrasonic scalpel should be provided with a transducer detecting the depth of the low-temperature effect on the tissue being dissected, which should be located inside a second pipeline with a round cross-section, which is hermetically sealed inside the tubular heat exchanger throughout the length thereof on the wall opposite to the cutting device.

It is advisable that the low-temperature depth transducer should comprise a coaxial line located inside the second pipeline and coaxially therewith and secured on dielectric supports, a length of the internal conductor of said coaxial line, extending outside the internal conductor, should be located inside a dielectric bushing hermetically sealing the second cylindrical pipeline and function as a probe of the transducer, whose length should be selected from a range of one to two diameters of the second pipeline.

It is advisable that the dielectric bushing should be made from sapphire.

BRIEF DESCRIPTION OF THE ACCOMPANYING DRAWINGS

These and other objects of the invention will become apparent from the following description of preferred embodiments and accompanying drawings wherein:

FIG. 1 shows a longitudinal cross-section of a general view of a cryogenic ultrasonic scalpel, according to the invention;

FIG. 2 shows a view taken along arrow A of FIG. 1.

FIG. 3 shows the scalpel of FIG. 1 featuring a cutting device made as a plate, the housing being removed, according to the invention;

FIG. 8 shows a view taken along the line VIII—VIII of the scalpel of FIG. 1.

FIG. 9 shows the scalpel of FIG. 8 equipped with another embodiment of the cutting device, according to the invention;

FIG. 10 shows the scalpel of FIG. 8 featuring thermal insulation made as a layer of plastic material, according to the invention;

FIG. 11 shows the scalpel of FIG. 1, a view taken along the line XI—XI.

DETAILED DESCRIPTION OF THE INVENTION

Figure 4:
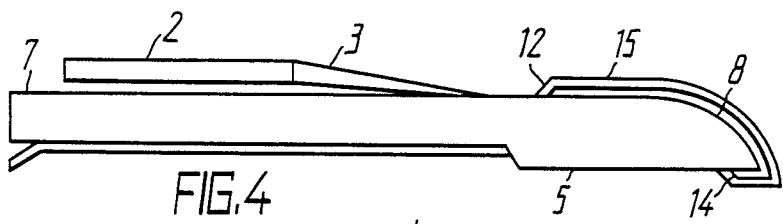
FIG. 4 shows the scalpel of FIG. 1 featuring a cutting device made as a hook, the housing being removed, according to the invention.

A cryogenic ultrasonic scalpel (FIGS. 1 and 2) comprises, according to the invention, an ultrasonic source 2 installed in a housing 1. The ultrasonic source 2 may be of any known type: piezoelectric, ferrite or metallic made of magnetostrictive alloys. A transformer 3 intended to transmit ultrasonic vibrations to a cutting device 4 is connected to the ultrasonic source 2. The scalpel also comprises a tubular heat exchanger 5 equipped with inlet and outlet pipes 6 and 7 for the refrigerant. Thermal insulation is provided between the cutting device 4 and the heat exchanger 5 in a gap 8 specially left between them throughout the length of the cutting device 4.

Thermal insulation is made by any known method, the simpliest being air, when an air gap 8 is provided between the heat exchanger 5 and the cutting device 4. Other variants will be described below for thermal insulation of these parts of the scalpel.

Thermal insulation makes it possible to keep the temperature of the cutting device 4 positive and separate, in space and time, from the ultrasonic and low-temperature actions on the tissue being dissected.

The cutting device 4 is made as a bent plate 9 (FIG. 3) having one end 10 thereof secured to the tubular heat exchanger 5. Thermal insulation, gap 8, is provided between the plate 9 and the heat exchanger 5. The transformer 3 is connected to the tubular heat exchanger 5.

Referring to FIG. 1, there is one more embodiment of a cutting device 4 which is a plate 11 whose one end 12 is secured to the transformer 3 and which forms a gap 8 with the heat exchanger 5 for heat insulation.

The cutting device 4 (plate 9 or 11) has a cutting edge 13 (FIGS. 2,3). The other end 14 of the plate 9 or 11 is free. The length of the plate 9,11 exceeds the length of the heat exchanger 5 (FIG. 2) or is equal thereto (FIG. 3). In both cases the plate 9,11 envelops the heat exchanger 5 totally or partially.

In another embodiment of the scalpel, the end 14 of the cutting device 4 made as a hook 15 (FIG. 4) is secured on the heat exchanger 5. The hook 15 also envelops the heat exchanger 5.

Figure 5:
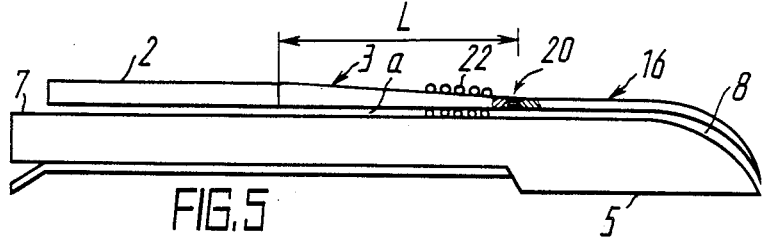
FIG. 5 shows the scalpel of FIG. 1 with the housing removed and provided with a unit combining the transformer and the cutting device, according to the invention.

A plate 16 in the embodiment of the scalpel shown in FIG. 5 envelops the heat exchanger 5 only partially, since the length of the plate 16 is equal to that of the heat exchanger 5.

It is important that whatever the embodiment of the cutting device 4, be it made as a plate 9,11, 16 or a hook 15, there is always a gap 8 (FIGS. 1-5) between the cutting device 4 and the heat exchanger 5.

FIG. 1 illustrates an embodiment of the heat exchanger 5 made as coaxially arranged tubes 17 and 18, ribs 19 being provided on the internal surfaces of these tubes 17 and 18 in order to increase this surface for heat exchange with the refrigerant.

For more effective separation of ultrasonic and low-temperature actions on the tissue being dissected, the plate 16 (FIG. 5) is rigidly secured to the transformer 3 which, in turn, is rigidly secured to the ultrasonic source 2 and they all together form a single unit located at a distance "a" from the heat exchanger 5. The gap 8, therefore, provides thermal insulation of the plate 16 from the heat exchanger 5 and extends to the end of the pipes 6 and 7 of the heat exchanger 5 which is thus insulated from the heat of the scalpel parts receiving ultrasonic vibrations, that is from the unit combining the ultrasonic source 2, the transformer 3, and the plate 16.

The cutting device, e.g. the plate 16 (FIG. 5), is made detachable and is rigidly secured to the transformer 3 by any known method, e.g. by a threaded connection 20.

Losses of ultrasonic power at the connection of the detachable cutting device, e.g. the plate 16 (FIG. 5), are minimal when the length of said cutting plate 16 is divisible by an uneven number of quarter wavelengths of ultrasonic vibrations and, also, when the place where the cutting device is secured to the transformer 3 is selected on the basis of the following condition:

$$L = \frac{\lambda(2n + 1)}{4}, \tag{1}$$

where

L is the distance from the ultrasonic source 2 to the place where the plate 16 is secured;

$\lambda$ is the ultrasonic wavelength in the transformer 3;

n is the number of ultrasonic halfwaves which can be fit into the distance from the ultrasonic source 2 to the place where the detachable plate 16 is secured on the transformer 3.

Figure 6:
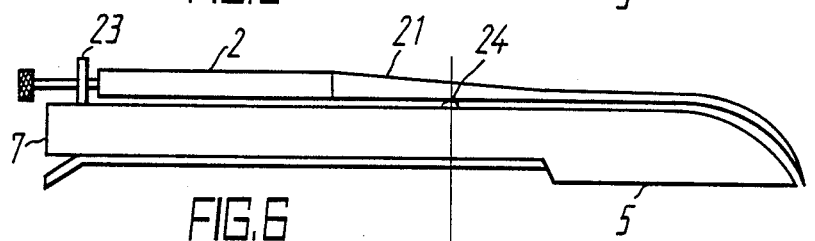
FIG. 6 shows an embodiment of a cryogenic ultrasonic scalpel equipped with a cutting device and transformer made of the same material, according to the invention.

The plate 16 and the transformer 3 are made as a single part 21 (FIG. 6) from the same material. This helps reduce ultrasonic power losses on the way to the plate 16 and thus raise the effectiveness of cutting.

In all embodiments the thickness of the cutting device varies along the length thereof.

When the ultrasonic source 2, the transformer 3, and the plate 16 are made as a single unit, the positive temperature of the cutting device which is the plate 16 (FIGS. 5 and 6) is kept by installing a heating element 22, e.g. an electrical spiral element, on the transformer 3.

The gap 8 may be either fixed (FIGS. 1,3,4,5) or adjustable (FIG. 6) by means of, for example, a variable eccentric device 23 (FIG. 6) inserted between the ultrasonic source 2 and the pipe 7. Other devices may also be used for this purpose in a similar manner.

The gap 8 (FIGS. 1 and 3-6) is selected from a range 0.5-4 mm. If the gap 8 is less than 0.5 mm, the low-temperature effect of the heat exchanger 5 is transmitted to the cutting device 4 cooling it to negative temperatures (Centigrade), which adversely affects the efficiency of cutting. If the gap 8 exceeds 4 mm, the time lag between the ultrasonic and low-temperature actions becomes too long and the hemostatic effect deteriorates.

For operations on the liver, the gap 8 should be preferably equal to 2 mm.

A fixing element 24 (FIG. 6) made of a heat-insulating material is provided between the tubular heat exchanger 5 and the unit combining the transformer 3 with the cutting device 4 in order to keep a desired gap 8. The fixing element 24 is installed in the point "b" (FIG. 7) of a standing ultrasonic wave 25 produced in the transformer 3 and the plate 16 when excited by the source 2.

Figure 7:
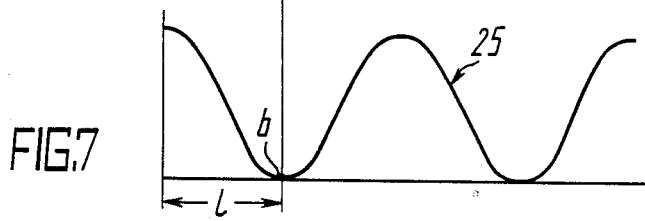
FIG. 7 shows a cryogenic ultrasonic scalpel and an ultrasonic wave diagram matched therewith, according to the invention.

Referring to FIG. 7, the amplitude of the ultrasonic standing wave 25 is plotted on the vertical axis, while the distance from the ultrasonic source 2 to each part of the unit 21 combining the transformer 3 and the cutting device 4 is plotted on the horizontal axis.

In this embodiment the fixing element 24 is installed in the first, from the ultrasonic source 2, at point "b" of the standing ultrasonic wave 25. But the fixing element 24 may also be placed at a different distance from the ultrasonic source 2, which can be found from the following equation:

$$l = \frac{\lambda(2n-1)}{4}, \quad (2)$$

where
l is the distance to the fixing element 24 from the ultrasonic source 2;
$\lambda$ is the length of the ultrasonic wave 25 in the transformer 3 and the plate 16;
n is the number of ultrasonic halfwaves which can be fit into the distance from the ultrasonic source 2 to the place where the fixing element 24 is installed.

Each element 19 intended to increase the heat exchanging surface with the refrigerant and, consequently, reduce the consumption of this refrigerant when maintaining a certain low-temperature level is selected so that the ratio c/d, where c is the thickness of the element 19 and d is its length, falls within a range from 0.1 to 0.2. It should be pointed out that, if the c/d ratio is less than 0.1, the tissue being dissected starts sticking to the tubular heat exchanger 5 because its cooling capacity becomes insufficient to freeze the dissected tissue at a high rate since the elements 25 are too thin. If the c/d ratio is more than 0.2, the tissue again starts sticking to the tubular heat exchanger 5 but for a different reason, a gas layer being formed on the elements 19 and affecting the cooling capacity of the heat exchanger 5.

The optimal c/d ratio is thought to be 0.15.

Besides, to increase the heat exchange surface, another ratio $S_1/S_2$ is to be selected, where $S_1$ is the area of the lateral surfaces of all elements 19 and $S_2$ is the area of the internal surface of the heat exchanger 5. The selection range is from 2 to 5.

In this case, if the $S_1/S_2$ ratio is less than 2, the rate of tissue dissection is slowed down because the cooling capacity of the tubular heat exchanger 5 becomes insufficient. In case the $S_1/S_2$ ratio exceeds 5, the dissected tissue may stick to the tubular heat exchanger 5 because the elements 19 occupy too much surface on the walls of the heat exchanger 5 and the hydraulic resistance to the refrigerant grows, thus affecting the cooling capacity of the tubular heat exchanger 5.

The tubular heat exchanger 5 has a cross section shaped as a trapezium 26 as shown in FIGS. 8-10. A shorter base 27 of the trapezium 26 faces the cutting device 4 and its shape repeats, throughout the length of the cutting device 4, the shape of this cutting device 4 as shown in FIG. 2 where it is tapering along the length thereof.

The lateral surfaces of the tubular heat exchanger 5 are in line with the lateral surfaces of the cutting device 4, 28, 29 (FIGS. 8-10) so that extensions of the sides of the trapezium 26 coincide, at their interactions, with the cutting edge 13 of the cutting device 4 (FIG. 8) or 28 (FIG. 9) or 29 (FIG. 10).

The sides of the trapezium 26 may be straight as in FIGS. 8 and 10, or concave as in FIG. 9.

The edge of the cutting device 4, which is opposite to the cutting edge 13 (FIG. 8), has rounded angles.

The cutting device 28 (FIG. 9) has a sharp edge 30 opposite to the cutting edge 13 in order to improve the contact of the lateral surfaces of the tubular heat exchanger 5 with the tissue being dissected.

A layer of a plastic material 31 is provided between the cutting device 29 (FIG. 10) and the tubular heat exchanger 5. This plastic material 31 should have low thermal conductivity and possess water-repelling properties. It may, for example, be a fluorine-bearing material. The layer 31 of this plastic material makes the structure of the device more rigid while retaining thermal insulation between the tubular heat exchanger 5 and the cutting device 29. Lateral surfaces 32 of the plastic layer 31 mate lateral surfaces of the tubular heat exchanger 5 with the surfaces of the cutting device 29.

The cryogenic ultrasonic scalpel according to the invention is provided with a temperature transducer 33 (FIG. 11) of the tubular heat exchanger 5 in the zone of contact with the tissue being dissected and a low-temperature depth transducer 34. These transducers are provided to ensure optimal selection of cutting speed by controlled low-temperature action on the dissected tissue and maintaining desired ultrasonic and low-temperature conditions during dissection of tissues.

The temperature transducer 33 is installed in a pipe 35 provided in the tubular heat exchanger 5 throughout its length on the wall which is the larger base of the trapezium 26 (FIGS. 8-10) and is hermetically sealed in relation to the internal space of the tubular heat exchanger 5 (FIG. 11). The cross section of the pipe 35 is arbitrary, e.g. in this embodiment the pipe 35 is round. The temperature transducer 33 is secured in the pipeline 35 by means of a bushing 36 made from a heat-conducting material, e.g. epoxy compound with a filler. Output conductors 37 from the temperature transducer 33 run inside the pipe 35. The temperature transducer 33 may be any of the following devices: a temperature-sensitive resistor, a thermocouple, a bolometer or any other temperature-sensitive instrument fit to operate in a temperature range from 77 to 300 K. The temperature transducer 33 should be placed to monitor the temperature in the zone where the tubular heat exchanger 5 is no longer in contact with the tissue being dissected in order to obtain reliable information on the temperature of the dissected tissue.

The low-temperature depth transducer 34 is located in the other pipe 38 disposed inside and along the length of the tubular heat exchanger 5 on the same wall as the pipe 35. The pipe 38 has a round cross-section and is hermetically sealed from the inner space of the tubular heat exchanger 5. The inlet opening of the pipe 38 is sealed by a bushing 39. A coaxial cable is arranged inside the pipe 38 on dielectric supports 40. An internal conductor 41 of this coaxial cable extends beyond an external conductor 42 and is a probe 43 of the transducer 34 sensitive to the depth of the low-temperature effect of the scalpel on the tissue being dissected. The probe 43 is placed inside the dielectric bushing 39 made of sapphire. The probe 43 of the transducer 34 should have a length selected from a range from 1 to 2 diameters of the pipe 38.

If the length of the probe 43 is less than the diameter of the pipe 38, its sensitivity is too low and the transducer 34 cannot adequately monitor the low-temperature effect over the desired depth range. This adversely affects the efficiency of the scalpel.

When the length of the probe 43 is more than two diameters of the pipe 38, errors of the sensing device increase and the efficiency of the scalpel is also adversely affected thereby.

The optimal length of the probe 43 should preferably be 1.4 of the diameter of the pipe 38.

A heating element 44 (FIG. 1) is provided inside the housing 1 on the internal surface thereof to warm this housing 1 and ensure a comfortable temperature of the housing 1 for an operator. The heating element 44 may be of any known type, but the most efficient, probably, is a ribbon or strip heating element.

Figure 12:
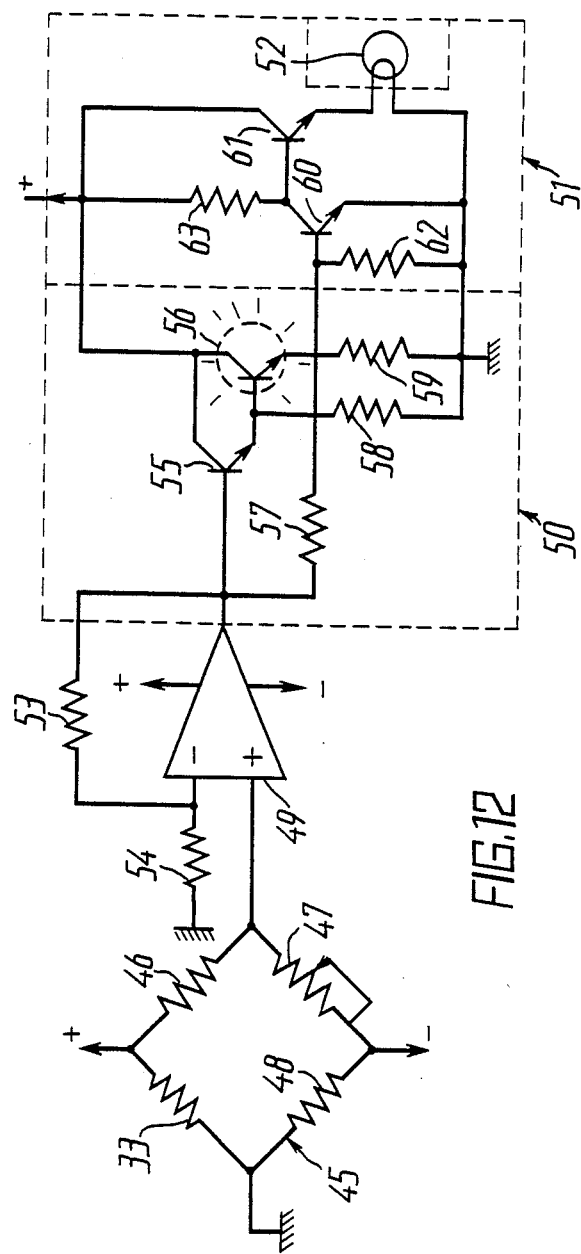
FIG. 12 shows an electrical circuit diagram of a temperature sensor, according to the invention.

Referring to FIG. 12, the circuit for monitoring the temperature of the tubular heat exchanger 5 employs a resistance transducer 33. This resistance transducer 33 is inserted into a bridge circuit 45 made up of resistors 46, 47, and 48, constant voltage being applied to one of the diagonal arms of the bridge, connecting two opposite corners thereof. The out-of-balance signal of the bridge circuit 45, which is generated when the resistance of the transducer 33 changes, is supplied to a voltage amplifier 49 whose output is connected to a power amplifier 50 and an amplifier 51 loaded into an indicator lamp 52.

The amplifier 49 is an operational amplifier featuring resistors 53 and 54 in the feedback circuit and on the inverting input.

The amplifier 50 is built around transistors 55 and 56 and resistors 57 and 58 and is equipped with a load resistor 59.

The amplifier 51 is built around transistors 60 and 61 and resistors 62 and 63.

For operations on soft tissues and parenchimal organs the working temperature of the tubular heat exchanger 5 is kept at a desired level by the above described circuit (FIG. 12). But, nevertheless, this cannot help maintain the desired level of low-temperature action on different tissues because of their anatomical peculiarities. Thus, for example, the depth of the low-temperature action is less in tissues whose blood supply is larger as compared to tissues with meager blood supply. In the first instance the low-temperature effect may be insufficient for hemostasis, while in the latter case a vast area of postoperational necrosis may result because the depth of freezing is more than needed. To monitor the depth of the low-temperature effect on the tissue being dissected, the proposed cryogenic ultrasonic scalpel is provided with a transducer 34.

Figure 13:
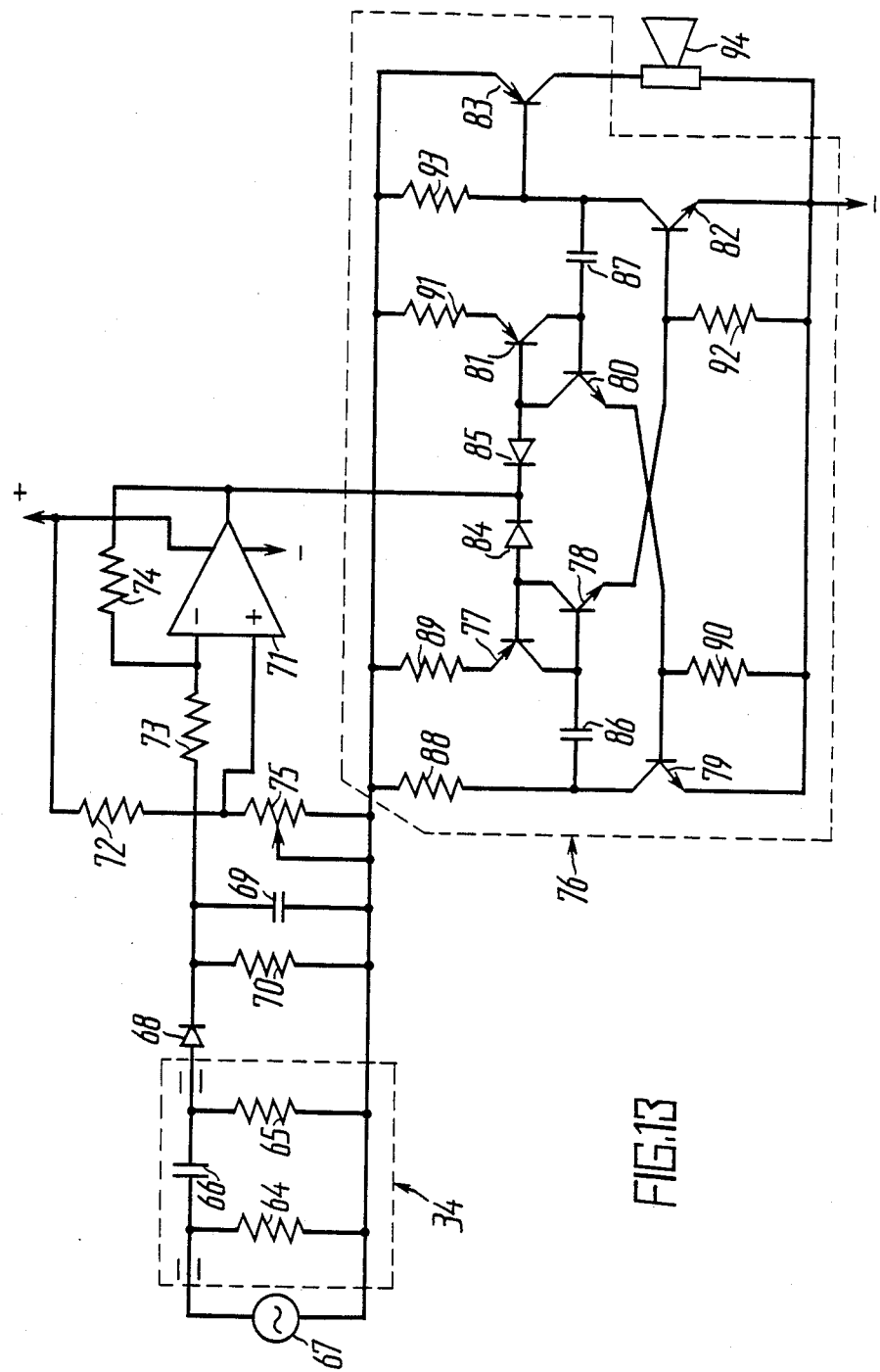
FIG. 13 shows an electrical circuit diagram of a low-temperature depth transducer, according to the invention.

Referring to FIG. 13, the diagram shows a connection circuit of the transducer 34 for monitoring the depth of the low-temperature action. The transducer 34 comprises resistors 64 and 65 and a capacitor 66. It is connected to a variable high-frequency source 67 and to a diode 68. The output of the diode 68 is loaded to an RC-circuit 69, 70 and connected to an input of an operational amplifier 71 comprising resistors 72, 73, 74 and a master variable resistor 75. The output of the operational amplifier 71 is connected to an input of an audiofrequency generator 76 built in the known arrangement employing transistors 77, 78, 79, 80, 81, 82, 83, diodes 84 and 85, capacitors 86 and 87, and resistors 88, 89, 90, 91, 92, and 93. The output of the audio-frequency generator 76 is connected to an electrodynamic loudspeaker 94.

The cryogenic ultrasonic scalpel is prepared for operation as follows.

The refrigerant, e.g. liquid nitrogen, is supplied via the pipeline 6 (FIG. 1) in the direction of the arrow 95 to the tubular heat exchanger 5. The refrigerant leaves the pipe 17, flows over the inner walls of the tubular heat exchanger 5 and elements 19 arranged therein, and is removed, as a liquid-vapour mixture, from the space of the tubular heat exchanger 5 through the pipe 18 and pipeline 7 in the direction indicated by arrows 96.

Initially, when the refrigerant is only started to be supplied, the heat exchanger 5 has a positive temperature and the bridge circuit 45 is unbalanced to a maximum because the resistances of the transducer 33 and resistor 47 are not equal. The resistor 47 is variable and, consequently, the temperature of the heat exchanger 5 can be controlled within a range from 80 to 150 K. The out-of-balance signal of the bridge circuit 45 is fed to the amplifier 49, then to the power amplifier 50, and, in this way, ensures the heating of the load resistor 59, which results in an increase in the supply of the refrigerant to the tubular heat exchanger 5 and initiates intensive cooling of the heat exchanger 5. Simultaneously, the output voltage of the amplifier 49 disables the output stage of the amplifier 51. As the heat exchanger 5 cools down, the out-of-balance signal diminishes and the heat power produced by the load resistor 59 decreases, less refrigerant is supplied to the heat exchanger 5. When the heat exchanger 5 reaches its working temperature, the out-of-balance signal at the output of the bridge circuit 45 is reduced to zero. The resistor 59 is no longer heated and the lamp 52 flashes on indicating that the scalpel is ready for operation as far as the low-temperature action is concerned.

The period required for the cryogenic ultrasonic scalpel to reach the working temperature, when liquid nitrogen is used as a refrigerant, is equal to 1.5–3 minutes with the excess pressure in the supply tank being within a range from $0.2 \cdot 10^5$ Pa to $0.5 \cdot 10^5$ Pa.

When the heat exchanger 5 reaches its working temperature, the ultrasonic source 2 is turned on and surgical intervention can be started.

Resection of soft and paremchimal tissues by the cryogenic ultrasonic scalpel is performed by successive incisions of the target organ and separation of larger blood vessels since hemostasis can only be attained on vessels with a diameter of up to 2 mm. Isolated blood vessels having a larger diameter are dealt with, prior to dissection, by conventional surgical methods, e.g. by ligation in the incision plane.

Initially, the cutting device penetrates the tissue and it is exposed to ultrasonic action providing partial hemostasis. As the scalpel is propelled along the incision line, the tissue areas which had been exposed to ultrasonic action are now exposed to the low temperature from the heat exchanger, which adds to hemostasis by destruction of the dissected tissue. The angle between the longitudinal axis of the scalpel and the tissue to be dissected is selected so that the zones exposed to ultrasonic and low-temperature effects overlap during dissection. Bleeding from blood vessels of up to 2 mm in diameter can be arrested. In the dissection area the tissue is frozen to the depth of 2.5 mm.

Further introduction of the scalpel into the frozen tissue is done as follows.

The cutting device which has a positive temperature comes into contact with the tissue and raises its temperature so that it is easily dissected by the sharp edge of the scalpel. Ultrasonic effect contributes to faster dissection of the frozen tissue and ensures hemostasis as described above. Stable hemostasis at a high dissection speed is ensured also by the gap 8 providing thermal insulation between the cutting device 4 and the tubular heat exchanger 5, whereby ultrasonic and low-temperature actions are separated in space and distributed in time and, simultaneously, the temperature of the cutting device is brought up to a level corresponding to positive temperatures of the tissue being dissected in the place where it comes into contact with the cutting edge of the cutting device. Depending on the anatomical peculiarities of the organ being operated on, stable hemostasis occurs at different tissue freezing depths. Since the gap 8 for thermal insulation between the cutting device 4 and the tubular heat exchanger 5 ensures high refrigerating performance of the scalpel, an optimal tissue freezing depth for each organ can be attained by means of transducers 33 and 34 monitoring the tissue freezing temperature and depth. As the tissue is being dissected, the freezing depth transducer 34 is used to keep a desired level of tissue freezing, which is sufficient for stable hemostasis and, at the same time, causing no post-operational necrosis in large areas of the dissected tissue.

The transducer 34 operates as follows. AC high-frequency voltage is supplied from the external source 67 via the internal coaxial cable made up of two conductors 41 and 42 to the transducer 34 (FIG. 13). Voltage induced in the external coaxial line made up of the conductor 42 and the pipe 38 as a result of the interaction of the high-frequency voltage with the tissue being dissected in the area of the probe 43 of the transducer 34 depends on the depth to which the tissue is frozen. This ac voltage is detected by the diode 68, amplified by the amplifier 71, and supplied to the controlled audio frequency generator 76. The frequency of the generator 76 is dictated by the signal fed from the transducer 34 sensing the freezing depth. When this signal deviates from the level set by the resistor 75, the frequency of the generator 76 goes down if the depth of the low-temperature action on the tissue being dissected is less than the assigned depth, or increase if the depth of the low-temperature action exceeds the assigned level. The desired level of the low-temperature action on the tissue being dissected is set by adjusting the resistor 75. The frequency of the signal generated by the loudspeaker 94 should remain unchanged to keep the freezing depth at the desired level during an operation.

Anatomical peculiarities of an organ being operated on may require that the gap 8 for thermal insulation between the cutting device 4 and the tubular heat exchanger 5 be adjusted. The gap 8 is to be made narrower when dealing with organs having intensive blood supply, and it is increased when the blood supply level is low. Adjustment of the gap 8 ensures an optimal balance between the ultrasonic and low-temperature actions on the tissue being dissected with a view to anatomical peculiarities of the organ being operated.

Numerous clinical trials and operations by cryogenic ultrasonic scalpels have demonstrated that their employment is extremely effective for surgical interventions on the liver and other parenchimal organs.

The cryogenic ultrasonic scalpel made according to the invention have been tested in experiments on eight dogs, where liver resections of different volume have been performed.

For supermedian laparotomy the left medial lobe of the liver was brought out of the incision and resection at the base of the lobe was performed. During the operation, an optimal level of cryoultrasonic action was selected, the freezing depth being kept at a level ensuring a dissection speed close to that of the conventional scalpel. No hemorrhage was observed during dissection. The freezing depth was about 2-2.5 mm, the temperature of tissue on the cut surface did not exceed $-140°$ C. When the dissected tissue was warmed up, some bleeding was observed from blood vessels with diameters in excess of 2 mm and additional ligation was necessary. No bleeding from smaller vessels was noticeable. Biochemical, thermometric, and morphological aspects have been studied dynamically. Healing of the wound was by first intention; no hemorrhages, bile secretion, peritonitis was observed. It has been found that this scalpel can be used with the cutting speed as a conventional scalpel for dissection of tissue portions of different toughness and different blood supply. It has also been found that tissue can be dissected at different angles of the scalpel to the tissue surface to a depth equal to the length of the cutting device. The tissue being dissected does not stick to the cutting device and complete hemostasis of blood vessels up to 2 mm in diameter is achieved. It has been also found that post-operational convalescence period is substantially reduced because it becomes possible to control the temperature and freezing depth during the operation and, consequently, to achieve optimal conditions by the use of the proposed cryogenic ultrasonic scalpel.

Clinical experience has demonstrated in five liver resections, including removal of lobes and halves because of parasitic deseases, such as alveococcosis, echinococcosis, tumors, and purulent processes. Trial data obtained previously for the effectiveness of the cryoultrasonic scalpel have been proved right. All patients have successfully undergone operations and recovered without complications. It has been found that the time required for an operation by the new scalpel was definitely shorter. Other advantages include a pronounced nemostatic effect (arresting of parenchimal bleeding), absence of additional injuries to the operated organ. The period of hospitalization has, on the average, been cut down by 15 days.

One of the advantages of the proposed cryogenic ultrasonic scalpel consists in that the thermal insulation provided between the cutting device 4 and the tubular heat exchanger 5 permits separation of ultrasonic and low-temperature actions in time and space. Hemostatic effect of ultrasonic vibrations is improved by the low temperature, increasing the rate of hemostasis. Besides, when a series of successive dissections is to be made, the cutting device 4 vibrating at an ultrasonic frequency and having a positive temperature easily dissects the tissue frozen by the previous cutting action, thus achieving a reliable hemostatic effect. With the higher rate of hemostasis and dissection, the time of operations where resections are made by the proposed scalpel can be substantially reduced.

Since heat inputs from the cutting device 4 to the tubular heat exchanger 5 are eliminated by introduction of thermal insulation, the rate of the low-temperature action on the tissue being dissected grows, as does the hemostatic effect, while the area of post-operational necrosis of the dissected tissue becomes much smaller.

The thermal insulation provided between the cutting device 4 and the tubular heat exchanger 5 permits a higher level of ultrasonic hemostatic action on the tissue being dissected because the subsequent low-temperature action removes the harmful heat influence of high-power ultrasonic vibrations. This is achieved by proper selection of the ratio between the ultrasonic power supplied to the cutting device 4 and the refrigeration capacity of the heat exchanger 5.

When the cutting device 4 is made as a plate 9 or hook 11 or 16, which have one or both ends thereof secure on the tubular heat exchanger 5 so that a gap 8 is left between them, tough portions of pathological tissue, e.g. calcareous portions, can be dissected. The dissection effort required in this case means that the cutting device 4 has to be rigidly secured on the heat exchanger 5 so that the gap 5 can be kept constant. The fixing element 24 may be provided for the purpose and installed in the point "b" of the ultrasonic standing wave 25 produced in the transformer 3 and in the cutting device 16 when ultrasonic vibrations are excited. A layer 31 of plastic material may also be provided for the same purpose in the gap 8. Water repelling properties of the plastic material ensure that the tissue being dissected does not stick thereto, since the plastic layer 31 is kept at an intermediate temperature between the negative temperature of the heat exchanger 5 and the positive temperature of the cutting device 4.

The fixing element 24 is placed in the point "b" of the standing wave 25 in order to reduce ultrasonic power losses. The same can be achieved when the transformer 3 and the cutting device 4 are combined into a single unit 21. In this case, they are installed with a gap 8 in relation to the tubular heat exchanger 5 and the pipes 6 and 7 thereof. No ultrasonic power is therefore lost for transfer to the heat exchanger 5. It has an additional advantage of reduced heat input to the tubular heat exchanger 5 from the ultrasonic source 2, which saves the refrigerant required to achieve a specific cooling capacity.

The cutting device 4 is equal in length or longer than the tubular heat exchanger 5 in order to provide a capability of dissecting tissue at different angles of the scalpel to the surface thereof. Thus, for example, the scalpel equipped with a cutting device made as the plate 9 equal in length to the tubular heat exchanger 5 is capable of dissecting tissue within a range from 45° to 80° by pulling motion. The scalpel wherein the cutting device is made as a hook 15 longer than the heat exchanger 5 is used with a negative tilt or in dissections by pushing motion. In all cases, complete overlap of ultrasonic and low-temperature zones has to be achieved in the tissue being dissected.

The scalpel, according to the invention, can be provided with a gap 8 between the cutting device 4 and the tubular heat exchanger 5, wherein elements 19 are installed to make the heat exchange surface larger. This scalpel has a higher refrigerating capacity and can be used for deep dissections while ensuring uniform low-temperature effect throughout the depth of the cut. Proper selection of the relation of the size of the elements 19 and the area of their lateral surfaces can help avoid formation of a gaseous refrigerant layer on the walls of the inner space of the heat exchanger 5, which reduces the cooling capacity of the heat exchanger 5 and results in a considerable temperature gradient along this heat exchanger 5. This cryo-ultrasonic scalpel exerts uniform low-temperature effect on the tissue being dissected even when the cutting device 4 penetrates into the tissue completely together with the heat exchanger 5. This helps reduce the post-operational necrosis area.

Transducers 33 and 34 provided in the scalpel to determine the temperature and freezing depth of the tissue being dissected offer the advantage of controlling the dissecting process and selecting optimal conditions for each particular case. In addition, it becomes possible to automatically maintain desired levels of ultrasonic and freezing effects on the tissue being dissected.

What is claimed is:

1. A cryogenic ultrasonic scalpel comprising:
   a housing intended to protect an operator's hand against effects of low temperatures and ultrasonic vibrations;
   an ultrasonic source arranged in said housing;
   a transformer connected to said ultrasonic source and arranged in said housing;
   cutting means for cutting biological tissue and arranged beyond said housing, said cutting means being connected to said transformer and receiving ultrasonic vibrations from said ultrasonic source via said transformer;
   tubular heat exchanger means, arranged beyond said housing and having a lateral surface and an internal space, for producing a low-temperature effect on the tissue being cut;
   inlet pipe means for supplying a refrigerant to said tubular heat exchanger means and arranged in said housing;
   outlet pipe means for removing the refrigerant from said tubular heat exchanger means and arranged in said housing; and heat insulation means disposed between said tubular heat exchanger means and said cutting means for protecting said cutting means against low-temperature effects of said heat exchanger means.

2. A cryogenic ultrasonic scalpel as claimed in claim 1, comprising said cutting means made as a plate having at least one cutting edge; said plate secured on said tubular heat exchanger means and forming a gap with said surface of said tubular heat exchanger means to provide said mutual thermal insulation.

3. A cryogenic ultrasonic scalpel as claimed in claim 1, comprising said cutting means made as a hook having at least one cutting edge, a first end and a second end, and secured on said tubular heat exchanger means by said first end; said hook forming a gap with said surface of said tubular heat exchanger means to provide said mutual thermal insulation.

4. A cryogenic ultrasonic scalpel as claimed in claim 1, wherein said cutting means is rigidly secured on said transformer and which has a single unit made up of said ultrasonic source rigidly connected to said transformer and said cutting means; said single unit disposed at a distance from said tubular heat exchanger means and from said refrigerant outlet pipe means and providing said mutual thermal insulation.

5. A cryogenic ultrasonic scalpel as claimed in claim 1, comprising a plurality of means for increasing the heat-exchanging surface of the refrigerant with said tubular heat exchanger means, which are installed inside said internal space of said tubular heat exchanger means.

6. A cryogenic ultrasonic scalpel as claimed in claim 1, wherein said tubular heat exchanger means has a cross-section shaped like a trapezium having a lesser base and a greater base, said lesser base facing said cutting means.

7. A cryogenic ultrasonic scalpel as claimed in claim 2, wherein said plate has a length equal to the length of said tubular heat exchanger means.

8. A cryogenic ultrasonic scalpel as claimed in claim 2, wherein said plate has a length exceeding the length of said tubular heat exchanger means.

9. A cryogenic ultrasonic scalpel as claimed in claim 2, wherein said cutting means is equipped with a device for travelling with respect to said tubular heat exchanger means, which is used to adjust said gap between said cutting means and said tubular heat exchanger means.

10. A cryogenic ultrasonic scalpel as claimed in claim 2, wherein the thickness of said cutting means varies along the length thereof.

11. A cryogenic ultrasonic scalpel as claimed in claim 2, wherein said gap is selected from a range from 0.5 mm to 4 mm.

12. A cryogenic ultrasonic scalpel as claimed in claim 3, wherein said hook is secured on said tubular heat exchanger means by said second end thereof.

13. A cryogenic ultrasonic scalpel as claimed in claim 3 wherein the length of said hook is equal to the length of said tubular heat exchanger means.

14. A cryogenic ultrasonic scalpel as claimed in claim 3, wherein the length of said hook exceeds the length of said tubular heat exchanger means.

15. A cryogenic ultrasonic scalpel as claimed in claim 3, wherein said cutting means is equipped with a device for travelling with respect to said tubular heat exchanger means, which is used to adjust said gap between said cutting means and said tubular heat exchanger means.

16. A cryogenic ultrasonic scalpel as claimed in claim 3, wherein said gap is selected from a range from 0.5 mm to 4 mm.

17. A cryogenic ultrasonic scalpel as claimed in claim 4, wherein said cutting means and said transformer are made of the same material as a single unit.

18. A cryogenic ultrasonic scalpel as claimed in claim 4, wherein said cutting means is made detachable so that it can be replaced and is provided with a means for being secured on said transformer.

19. A cryogenic ultrasonic scalpel as claimed in claim 4, comprising a first heating element installed on said transformer to keep the temperature of said cutting means positive in degrees Celcius.

20. A cryogenic ultrasonic scalpel as claimed in claim 4, comprising a fixing element made of a heat-insulating material and disposed on said refrigerant outlet pipe means at a distance from said ultrasonic source, which is equal to the product of a quarter of the ultrasonic wavelength by a double-minus-one number of ultrasonic half-waves which can be fit into the distance on said transformer and said cutting means to the place where said fixing element is installed; said fixing element maintaining on a contant level said gap between said tubular heat exchanger means and said cutting means.

21. A cryogenic ultrasonic scalpel as claimed in claim 5, wherein the thickness of each said means for increasing the surface of heat exchange from said plurality of means is determined on the basis of its relation to the length of said means, which is selected from a range from 0.1 to 0.2.

22. A cryogenic ultrasonic scalpel as claimed in claim 5, wherein the ratio of the total area of the lateral surface of said plurality of means for increasing the heat-exchanging surface to the area of the internal surface of said tubular heat exchanger means is selected from a range from 2 to 5.

23. A cryogenic ultrasonic scalpel comprising:
a housing intended to protect an operator's hand against effects of low temperatures and ultrasonic vibrations;
an ultrasonic source arranged in said housing;
a transformer connected to said ultrasonic source and arranged in said housing;
cutting means for cutting biological tissue and arranged beyond said housing, said cutting means being connected to said transformer and receiving ultrasonic vibrations from said ultrasonic means via said transformer;
tubular heat exchanger means, arranged beyond said housing and having a lateral surface and an internal space for producing a low-temperature effect on the tissue being cut;
inlet pipe means for supplying a refrigerant to said tubular heat exchanger means and arranged in said housing;
outlet pipe means for removing the refrigerant from said tubular heat exchanger means and arranged in said housing;
said cutting means having lateral surfaces and having such a shape that said lateral surfaces are extensions of said lateral surface of said tubular heat exchanger means, the two lateral surfaces being inclined toward each other to form, at the intersection thereof, a cutting edge of said cutting means; and
heat insulation means located between said tubular heat exchanger means and said cutting means for protecting said cutting means against low-temperature effects of said heat exchanger.

24. A cryogenic ultrasonic scalpel as claimed in claim 2 or 3 or 23, wherein said portion of said lateral surface of said tubular heat exchanger means, which faces said cutting means, repeats the shape of said cutting means.

25. A cryogenic ultrasonic scalpel as claimed in claim 2 or 3 or 23, wherein said cutting means is sharpened on the side opposite said cutting edge.

26. A cryogenic ultrasonic scalpel as claimed in claim 1 or 2 or 23, comprising a second heating element disposed on said housing and providing a comfortable temperature of said housing for an operator irrespective of the low-temperature action of said tubular heat exchanger means on said housing.

27. A cryogenic ultrasonic scalpel as claimed in claim 2 or 3 or 23, comprising a layer of a plastic material having heat-insulating and water-repelling properties.

28. A cryogenic ultrasonic scalpel as claimed in claim 1 or 2 or 3 or 23, comprising a first pipe which is hermetically sealed and arranged inside said internal space of said tubular heat exchanger means throughout the length of said tubular heat exchanger means on the wall opposite said cutting means; a temperature transducer of said tubular heat exchanger means in the zone of contact with the tissue being dessected, which is placed inside said first pipe.

29. A cryogenic ultrasonic scalpel as claimed in claim 1 or 2 or 3 or 23, comprising a second pipe having a round cross-section, hermetically sealed and installed in said internal space of said tubular heat exchanger means throughout the length of said tubular heat exchanger means on the wall opposite said cutting means; a transducer of the depth of the low-temperature action on the tissue being dissected, which is placed inside said second pipe.

30. A cryogenic ultrasonic scalpel as claimed in claim 28, comprising a second pipe having a round cross-section, hermetically sealed and arranged inside said internal space of said tubular heat exchanger means throughout the length of said tubular heat exchanger means on the same wall as said first pipe; a transducer of the depth of the low-temperature action on the tissue being dissected, which is located inside said second pipe.

31. A cryogenic ultrasonic scalpel as claimed in claim 29, wherein said transducer of the depth of the low-temperature action on the tissue being dissected comprises a coaxial cable arranged within said second pipe which is made cylindrical and coaxial therewith, said coaxial cable having an internal conductor and an external conductors; a dielectric bushing sealing said second pipe on the side facing the tissue being dissected during an operation; dielectric supports placed inside said second pipe, which are used to secure said external conductor of said coaxial cable inside said second pipe; a portion of said internal conductor of said coaxial cable, which extends beyond the limits of said external conductor and is a probe of said transducer of the low-temperature depth.

32. A cryogenic ultrasonic scalpel as claimed in claim 31, wherein the length of said probe is selected from a range from one to two diameters of said second pipe.

33. A cryogenic ultrasonic scalpel as claimed in claim 31, wherein said dielectric bushing is made of sapphire.

* * * * *

UNITED STATES PATENT AND TRADEMARK OFFICE
CERTIFICATE OF CORRECTION

PATENT NO. : 4,832,022

DATED : May 23, 1989

INVENTOR(S) : Gennady I. Tjulkov, et al

It is certified that error appears in the above-identified patent and that said Letters Patent is hereby corrected as shown below:

Title page:

Item [73] Assignees: please change "both of Moscow, U.S.S.R." to --both of Tomsk, U.S.S.R.--.

Signed and Sealed this

Twenty-first Day of August, 1990

Attest:

HARRY F. MANBECK, JR.

*Attesting Officer*  *Commissioner of Patents and Trademarks*